(12) United States Patent
Sunkara et al.

(10) Patent No.: US 7,745,668 B2
(45) Date of Patent: Jun. 29, 2010

(54) PROCESSES FOR REDUCING COLOR IN POLYTRIMETHYLENE ETHER GLYCOL POLYMERS

(75) Inventors: Hari Babu Sunkara, Hockessin (DE); Hiep Quang Do, Hillsborough, NJ (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 136 days.

(21) Appl. No.: 11/833,453

(22) Filed: Aug. 3, 2007

(65) Prior Publication Data

US 2007/0276164 A1 Nov. 29, 2007

Related U.S. Application Data

(60) Continuation-in-part of application No. 11/271,299, filed on Nov. 10, 2005, now Pat. No. 7,294,746, which is a division of application No. 10/634,687, filed on Aug. 5, 2003, now Pat. No. 7,009,082.

(60) Provisional application No. 60/468,226, filed on May 6, 2003.

(51) Int. Cl.
*C07C 43/11* (2006.01)

(52) U.S. Cl. ................................ 568/621; 568/619

(58) Field of Classification Search ........................ None
See application file for complete search history.

(56) References Cited

U.S. PATENT DOCUMENTS

| | | |
|---|---|---|
| 1,478,985 A | 12/1923 | Jacque |
| 2,315,584 A | 4/1943 | Borglin |
| 2,520,733 A | 8/1950 | Morris et al. |
| 3,326,985 A | 6/1967 | Mason et al. |
| 4,213,000 A | 7/1980 | Coates |
| 4,243,831 A | 1/1981 | Malloy et al. |
| 4,885,410 A | 12/1989 | De Thomas |
| 5,527,973 A | 6/1996 | Kelsey |
| 5,633,362 A | 5/1997 | Nagarajan et al. |
| 5,686,276 A | 11/1997 | Laffend et al. |
| 5,821,092 A | 10/1998 | Nagarajan et al. |
| 6,111,137 A | 8/2000 | Suizu et al. |
| 6,235,948 B1 | 5/2001 | Sunkara et al. |
| 6,245,844 B1 | 6/2001 | Kurian et al. |
| 6,720,459 B2 | 4/2004 | Sunkara et al. |
| 6,977,291 B2 | 12/2005 | Sunkara et al. |
| 7,009,082 B2 | 3/2006 | Sunkara et al. |
| 7,084,311 B2 | 8/2006 | Sunkara et al. |
| 2002/0010374 A1 | 1/2002 | Sunkara et al. |
| 2005/0225107 A1 | 10/2005 | Mitchell et al. |
| 2005/0225163 A1 | 10/2005 | Boll |

FOREIGN PATENT DOCUMENTS

| | | |
|---|---|---|
| DE | 3917645 | 6/1988 |
| EP | 0 657 529 | 12/1993 |

OTHER PUBLICATIONS

S.V. Conjeevaram, R.S. Benson, and D.J. Lyman, Department of Materials Science and Engineering, University of Utah, Salt Lake City, Utah 84112, Journal of Polymer Science: Polymer Chemistry Edition, vol. 23, 429-444 (1985).
S.M. Ghoreishi and M.R. Haghighi, Characterization and Reduction of Chromophores in Pulp Mill Effluents, Scientic Iranica, vol. 4, No. 3, pp. 131-138, Sharif University of Technology, Oct. 1997.
Herbert O. House, Modern Synthetic Reactions (second edition), W.A. Benjamin, Inc., Menlo Park, California, Reading, Massachusetts, London, Amsterdam, Don Mills, Ontario, Sydney, 1972.
PCT/US04/14042 International Search Report Written Opinion of the International Searching Authority dated Nov. 18, 2004.
Lewis Sr., Richard J., Hawley's Condensed Chemical Dictionary, twelfth edition, 1993, 218-219.

*Primary Examiner*—Rosalynd Keys
(74) *Attorney, Agent, or Firm*—Gail D. Tanzer

(57) ABSTRACT

Processes for reducing color in PO3G are provided. The processes include contacting PO3G with an activated carbon and then separating the PO3G from the activated carbon by, for example, filtration. The process provides PO3G having an APHA color less than that before contact with the absorbent. The processes are desirably used for polymers having a molecular weight of about 250 to about 5000.

16 Claims, No Drawings

PROCESSES FOR REDUCING COLOR IN POLYTRIMETHYLENE ETHER GLYCOL POLYMERS

PRIORITY

This application claims priority from Provisional U.S. patent application Ser. No. 60/468,226, filed May 6, 2003, and is a continuation-in-part of application Ser. No. 11/271,299, filed Nov. 10, 2005, now allowed, which is a divisional of application Ser. No. 10/634,687, filed Aug. 3, 2003, now U.S. Pat. No. 7,009,032, the disclosures of each of which are hereby incorporated herein by reference.

FIELD OF THE INVENTION

This invention relates to reduction of color of polytrimethylene ether glycol using activated carbon.

BACKGROUND 1,3-Propanediol (also hereinafter termed "PDO") is a monomer useful in the production of a variety of polymers including polyesters, polyurethanes, polyethers, and cyclic compounds. Homo and copolyethers of polytrimethylene ether glycol (hereinafter termed "PO3G") are examples of polyether polymers. The polymers are ultimately used in various applications including fibers, films, etc.

Chemical routes to generate 1,3-propanediol are known. For instance, 1,3-propanediol may be prepared from:

1. ethylene oxide over a catalyst in the presence of phosphine, water, carbon monoxide, hydrogen and an acid (the "hydroformylation rout");
2. the catalytic solution phase hydration of acrolein followed by reduction (the "acrolein route").

Both of these synthetic routes to 1,3-propanediol involve the intermediate synthesis of 3-hydroxypropionaldehyde (hereinafter also termed "HPA"). The HPA is reduced to PDO in a final catalytic hydrogenation step. Subsequent final purification involves several processes, including vacuum distillation.

Biochemical routes to 1,3-propanediol have been described that utilize feedstocks produced from biological and renewable resources such as corn feed stock. Such PDO is hereinafter referred to as "biochemical PDO" or "biochemically-derived PDO". For example, bacterial strains able to convert glycerol into 1,3-propanediol are found in e.g., in the species *Klebsiella, Citrobacter, Clostridium*, and *Lactobacillus*. The technique is disclosed in several patents, including, U.S. Pat. Nos. 5,633,362, 5,686,276, and, most recently, U.S. Pat. No. 5,821,092, all of which are incorporated herein by reference. In U.S. Pat. No. 5,821,092, Nagarajan et al. disclose, inter alia, a process for the biological production of 1,3-propanediol from glycerol using recombinant organisms. The process incorporates *E. coli* bacteria, transformed with a heterologous pdu diol dehydratase gene, having specificity for 1,2-propanediol. The transformed *E. coli* is grown in the presence of glycerol as a carbon source and 1,3-propanediol is isolated from the growth media. Since both bacteria and yeasts can convert glucose (e.g., corn sugar) or other carbohydrates to glycerol, the process of the invention provided a rapid, inexpensive and environmentally responsible source of 1,3-propanediol monomer useful in the production of polyesters, polyethers, and other polymers.

Precipitations (e.g., with 1,2-propylene glycol, as well as carboxylates or other materials) have been used since the early 1980's to separate the colored and odiferous components from desired products (such as enzymes) to obtain purified preparations. Precipitating the high molecular weight constituents from the fermentor liquors, then bleaching these components with a reducing agent (DE3917645) is known. Alternately, microfiltration followed by nanofiltration to remove the residual compounds has also been found helpful (EP657529) where substances with a high molecular weight above the size of separation are held back. However, nanofiltration membranes become clogged quickly and can be quite expensive.

Various treatment methods are disclosed in the prior art to remove color precursors present in the PDO, however, the methods are laborious, expensive and increase the cost of the polymer. For instance, Kelsey, U.S. Pat. No. 5,527,973, discloses a process for providing a purified 1,3-propanediol that can be used as a starting material for low color polyester. That process has several disadvantages including the use of large equipment and the need for dilution with large quantities of water, which are difficult to remove from the product. Sunkara et al., U.S. Pat. No. 6,235,948, discloses a process for the removal color-forming impurities from 1,3-propanediol by a preheating, preferably with heterogeneous acid catalysts such as perfluorinated ion exchange polymers. The catalyst is filtered off, and the 1,3-propanediol is then isolated, preferably by vacuum distillation. Preparation of polytrimethylene ether glycol from purified diol gave APHA values of 30-40, however, the molecular weight of the polymers were not reported.

The polyalkylene ether glycols are generally prepared by the acid-catalyzed elimination of water from the corresponding alkylene glycol or the acid-catalyzed ring opening of the alkylene oxide. For example, polytrimethylene ether glycol can be prepared by dehydration of 1,3-propanediol or by ring opening polymerization of oxetane using soluble acid catalysts. Methods for making PO3G from the glycol, using sulfuric acid catalyst, are described in. U.S. Pat. Nos. 6,977,291 and 6,720,459, the disclosures of which are incorporated herein by reference. It should be noted that polyol synthesis conditions largely determine amounts of impurities, color precursors, and color bodies formed. The polyether glycol prepared by the process is purified by the methods known in the art. The purification process for polytrimethylene ether glycol typically comprises (1) a hydrolysis step to hydrolyze the acid esters formed during the polymerization (2) water extraction steps to remove the acid catalyst, unreacted monomer, low molecular weight linear oligomers and oligomers of cyclic ethers, (3) a base treatment, typically with a slurry of calcium hydroxide, to neutralize and precipitate the residual acid present, and (4) drying and filtration of the polymer to remove the residual water and solids.

It is well known that the polytrimethylene ether glycol produced from the acid catalyzed polycondensation of 1,3-propanediol has quality problems, in particular the color is not acceptable to the industry. The polymer quality is in general dependent on the quality of the raw material, PDO. Besides the raw material, the polymerization process conditions and stability of the polymer are also responsible for discoloration to some extent. Particularly in the case of polytrimethylene ether glycol, the polyether diols tend to have light color, a property that is undesirable in many end-uses. The polytrimethylene ether glycols are easily discolored by contact with oxygen or air, particularly at elevated temperatures, so the polymerization is effected under a nitrogen atmosphere and the polyether diols are stored in the presence of inert gas. As an additional precaution, a small concentration of a suitable antioxidant is added. Preferred is butylated hydroxytoluene (BHT, 2,6-di-t-butyl-4-methylphenol) at a concentration of about 100-500 microg/g (micrograms/gram) polyether.

Also, attempts have been made to reduce the color of polytrimethylene ether glycols by conventional means without much success. For instance, Morris et al., U.S. Pat. No. 2,520,733, notes the peculiar discoloration tendency for the polytrimethylene ether glycol from the polymerization of PDO in the presence of acid catalyst. The many methods they tried that failed to improve the color of polytrimethylene glycols included the use of activated carbons, activated aluminas, silica gels, percolation alone, and hydrogenation alone. Consequently, they developed a process for the purification of polyols prepared from 1,3-propanediol in the presence of acid catalyst (2.5 to 6% by weight) and at a temperature from about 175° C. to 200° C. This purification process involves percolation of the polymer through Fuller's earth followed by hydrogenation. This extensive purification process gave a final product that was light yellow in color, in fact, this procedure yielded polytrimethylene ether glycol (Example XI therein) for which the color was only reduced to an 8 Gardner color, a quality corresponding to an APHA value of >300 and totally inadequate for current requirements.

Mason in U.S. Pat. No. 3,326,985 discloses a procedure for the preparation of polytrimethylene ether glycol of molecular weights in the range of 1200-1400 possessing improved color by vacuum stripping, under nitrogen, polytrimethylene ether glycol of lower molecular weight. The color levels, however, are not quantified and would not have approached the above requirement.

Malloy, et al., in U.S. Pat. No. 4,243,831, disclose the use of charcoal as an adsorbent to reduce the peroxides and color of olefins, which is a different class of chemicals than polytrimethylene ether glycol, and also uses different process condtions.

Morrell, et al., in U.S. Pat. No. 1,478,985, mention the possibility of the use of activated carbon to remove color from organic compounds, but is silent regarding specific process conditions and quantitation of color removal.

SUMMARY OF THE INVENTION

One aspect of the present invention is a process comprising contacting PO3G having an initial APHA color with activated carbon and separating the PO3G and activated carbon, wherein the PO3G, after contact with the activated carbon, has an APHA color lower than the initial color.

Another aspect of the present invention is a process comprising providing reactant comprising 1,3-propanediol and polycondensation catalyst; polycondensing the reactant to PO3G having an initial APHA color; contacting the PO3G with activated carbon; and separating the PO3G and activated carbon, such that the PO3G, after contact with the adsorbent, has an APHA color lower by at least about 10% than the initial color A further aspect of the present invention is a process comprising contacting PO3G with activated carbon and separating the PO3G and activated carbon, wherein the PO3G has an initial APHA color, before contact with activated carbon, of about 70 to about 300, and the PO3G, after contact with the activated carbon has an APHA color lower by at least about 10% than the initial color.

These and other aspects of the invention will be apparent to one skilled in the art in view of the following description and the appended claims.

DETAILED DESCRIPTION

Unless otherwise stated, all percentages, parts, ratios, etc., are by weight.

Trademarks are shown in upper case.

Further, when an amount, concentration, or other value or parameter is given as either a range, preferred range or a list of upper preferable values and lower preferable values, this is to be understood as specifically disclosing all ranges formed from any pair of any upper range limit or preferred value and any lower range limit or preferred value, regardless of whether ranges are separately disclosed.

In using the term "adsorbent", reference is made to materials that commonly are used to remove relatively small amounts of undesired components, whether such removal is by the process of adsorption or absorption, since many decolorization processes involve both mechanisms.

By the terms "color" and "color bodies" are meant the existence of visible color that can be quantified by the use of a spectrocolorimeter in the range of visible light, using wavelengths of approximately 400-800 nm, and by comparison with pure water. Color precursors in PDO are not visible in this range, but contribute color after polymerization.

The PO3G made from the PDO of the present invention can be PO3G homo- or co-polymer. For example, the PDO can be polymerized with other diols (below) to make co-polymer. The PDO copolymers useful in the present invention can contain up to 50% by weight (preferably 20% by weight or less) of comonomer diols in addition to the 1,3-propanediol and/or its oligomers. Comonomer diols that are suitable for use in the process include aliphatic diols, for example, ethylenediol, 1,6-hexanediol, 1,7-heptanediol, 1,8-octanediol, 1,9-nonanediol, 1,10-decanediol, 1,12-dodecanediol, 3,3,4,4,5,5-hexafluro-1,5-pentanediol, 2,2,3,3,4,4,5,5-octafluoro-1,6-hexanediol, 3,3,4,4,5,5,6,6,7,7,8,8,9,9,10,10-hexadecafluoro-1,12-dodecanediol, cycloaliphatic diols, for example, 1,4-cyclohexanediol, 1,4-cyclohexanedimethanol and isosorbide, polyhydroxy compounds, for example, glycerol, trimethylolpropane, and pentaerythritol. A preferred group of comonomer diol is selected from the group consisting of 2-methyl-1,3-propanediol, 2,2-dimethyl-1,3-propanediol, 2,2-diethyl-1,3-propanediol, 2-ethyl-2-(hydroxymethyl)-1,3-propanediol, 1,6-hexanediol, 1,8-octanediol, 1,10-decanediol, isosorbide, and mixtures thereof. Thermal stabilizers, antioxidants and coloring materials may be added to the polymerization mixture or to the final polymer if necessary.

In accordance with one aspect of the present invention, a process comprises contacting PO3G having an initial APHA color with adsorbent and separating the PO3G and adsorbent, wherein the PO3G, after contact with the adsorbent, has a APHA color lower than the initial color. Preferably, the APHA color is reduced by about 10%, more preferably, the color is reduced by 30% and most preferably, the color is reduced by about 50%. APHA color values are a measure of color as defined in ASTM-D-1209 (see Test Method 1, below).

The molecular weight of the PO3G is generally about 250 to about 10,000. Preferably, the molecular weight is about 500 to about 5000. In some preferred embodiments, the PO3G has a molecular weight of about 500 to about 4000.

Herein the term "activated carbon" includes "charcoal". Activated carbon is an amorphous solid that has very large internal surface area and pore volume and has very low affinity for water. The amount of adsorbent used depends on the nature of the adsorbent, concentration of color bodies in the polytrimethylene ether glycol, interaction with the substrate and the process conditions such as contact time and temperature. For instance, in the practice of the present invention, 0.1-5%, and preferably 0.25-3%, activated carbon based on the weight of the polyether glycol is added to the PO3G having color, with stirring under an inert atmosphere such as nitrogen.

The contacting of the PO3G with activated carbon is carried out at a temperature such that the polymer is liquid and has a viscosity low enough to permit mixing and stirring. The mixing and stirring can be carried out at temperatures of about 10-150° C., preferably, about 25-100° C. The contacting is conducted for a period of about 5 to about 60 min., and preferably about 10 to about 30 min. Preferably contacting the PO3G with the activated carbon and the subsequent filtration are completed under an inert nitrogen atmosphere.

Suitable processes for vacuum filtration are well known to those skilled in the art. Due to the viscosity of the PO3G, filtration is conveniently accelerated by filtering at an elevated temperature. Typically, a temperature in the range of about 50° to about 100° C. is sufficient. For small-scale preparations, a filter bed of CELPURE C65 is firmly packed onto a 1-micrometer Whatman filter paper, supported on a 250-mL fritted glass funnel, equipped with means to heat the filter. Other filter media can be used and will be well known to those skilled in the art, the requirements being a fineness of filter sufficient to retain the charcoal and inert to the glycol.

A batch process can be used, wherein the activated carbon is effectively contacted by mixing with the polyol and, after a period of time, separating the polyol from the activated carbon by a suitable method, for example, by filtration, centrifugation, etc. The process can also be conducted in a continuous or semi-continuous fashion. For example, the polyol can be pumped from a storage tank through a fixed bed of the activated carbon. The feed rate is adjusted for the kind, amount, and prior use of activated carbon in the bed and the color level of the feedstock so that the contact time of the polyol with the activated carbon is sufficiently long to give an effluent with the desired color reduction. The effluent can be kept in a holding tank for a short time, or used or shipped immediately. Other variations will be recognized by those skilled in the art.

The processes of the present invention can be used for the decolorization of polytrimethylene ether glycol prepared by polymerization of PDO prepared from petrochemical sources, such as the process using acrolien, and also to the polyol prepared by polymerization of PDO prepared by biochemical routes.

The activated carbon treatment can be performed on the polymer after purification, or it can be performed just prior to the filtration step of the purification process. It is preferable to add the activated carbon to PO3G polymer just prior to final filtration and store the filtered polymer in the presence of an antioxidant such as BHT.

Activated carbon is available from many sources in different forms such as powder, granular, and shaped products. The preferred form is powdered activated carbon.

Various brands of carbon can be used, including, but not limited to, Norit America G60, NORIT RO 0.8, Calgon PWA, BL, and WPH, and Ceca ACTICARBONE ENO. Other forms will be well known to those skilled in the art.

In another embodiment of the present invention, a process comprises:

(a) providing reactant comprising 1,3-propanediol and polycondensation catalyst;

(b) polycondensing the reactant to PO3G having an initial color;

(c) contacting the PO3G with activated carbon; and (d) separating the PO3G and activated carbon, such that the color of the PO3G, after contact with the activated carbon, has a APHA color lower I than the initial color. The APHA color after contact with the activated carbonis reduced preferably by at least about 10%, more preferably reduced by about 30% and most preferably reduced about 50% as compared to the initial color. Preferably, the PO3G is contacted with about 0.1 to about 5 weight % of the activated carbon based on the weight of the polytrimethylene ether glycol, and the contacting is conducted at a temperature of about 10° to about 150° C.

In accordance with a further aspect of the present invention, a product comprises (i) PO3G having color and (ii) activated carbon (as already described herein), wherein the PO3G has a APHA color of less than that before said contacting. Preferably, the APHA color is reduced by about 10%, more preferably, reduced by about 30% and most preferably, reduced by about 50%.—Also preferably, the product contains about 0.25% to about 5% activated carbon, more preferably about 1% to about 3% activated carbon.

Materials, Equipment, and Test Methods

The PO3G polymer prepared from 1,3-propanediol was obtained from DuPont or from a commercially available source. Activated carbons (DARCO, CALGON, and CECA) and BHT are from Aldrich Chemicals (Milwaukee Wis.). CELPURE products are from Advanced Minerals (Santa Barbara, Calif.). These products were used not only to remove color bodies from the polymer but also as filter aid.

Test Method 1. Color Measurement and APHA Values.

A Hunterlab ColorQuest Spectrocolorimeter [Reston, Va.] was used to measure the polymer color before and after solid adsorbent treatment. Color numbers of the polymer are measured as APHA values (Platinum-Cobalt System) according to ASTM D-1209. The polymer molecular weights are calculated from their hydroxyl numbers obtained from titration method (ASTM E1899-02).

EXAMPLES

The following examples are presented to demonstrate the invention, but are not intended to be limiting.

Example 1

Preparation of PO3G 1,3-Propanediol, 13.9 kg, and 139 g concentrated sulfuric acid were added to a 22-L glass reactor and the contents polymerized at 160° C. under nitrogen until the desired number average molecular weight was reached. In general, longer reaction times give polymers with higher molecular weight. A portion of the crude polymer (5 kg) and an equal volume of distilled water were transferred to another 22-L glass reactor with and the reaction mixture stirred slowly under a nitrogen blanket while heated to 100° C. for 4 hours. After 4 hours, the mixture was allowed to cool and separate into two phases by gravity. The aqueous phase was removed and discarded. The polymer once again was washed with water. The residual sulfuric acid present in the polymer was neutralized with an excess of calcium hydroxide. The polymer was dried under reduced pressure at 90° C. for 3 hours and then filtered through a Whatman filter paper precoated with a CELPURE filter aid. The purified PO3G polymer obtained was analyzed for molecular weight and color.

Example 2

Activated Carbon Treatment to Lower Polymer Color

A 250-mL fritted glass funnel was securely assembled. CELPURE C65 (4.4 g, 1.2 kg/m$^2$) was packed firmly on 1-micron size Whatman filter paper that was placed on the frit. A heating tape was wrapped around the funnel to provide heat to the polymer during filtration process. PO3G (80 g, MW=2400) was placed in a 250-mL round bottom flask. Activated carbon (0.008 g, 0.01 wt %, DARCO G60) was added to the polymer. A magnetic stir bar was added to the polymer that was then stirred on a stirrer for 10 minutes under nitrogen at room temperature. Then the polymer was filtered through the fritted glass funnel with the aid of house vacuum under a nitrogen blanket. The temperature was set at between 60° C.-70° C. by adjusting the temperature controller (VARIAC). The final polymer was measured for color on a Hunterlab ColorQuest Spectrocolorimeter. BHT (200 micrograms/g polymer) was added to the polymer after filtration is finished. A control measurement on a sample for which the activated carbon was omitted was made. The results are shown in Table 1.

Examples 3-5

The procedure of Example 2 was repeated using various amounts of DARCO G60 activated carbon. The molecular weight of the PO3G used in these examples was 2170. Results are also shown in Table 1.

TABLE 1

PO3G Color vs. Weight Percent of Activated Carbon

| Example | Wt % Activated Carbon | Polymer Color APHA |
| --- | --- | --- |
| Control | 0 | 126 |
| 2 | 0.01 | 121 |
| 3 | 0.05 | 104 |
| 4 | 0.15 | 96 |
| 5 | 0.25 | 88 |

The data in Table 1 show activated carbon removed color impurities in PO3G polymer and the color decreased with increase in amount of activated carbon from 0.01 to 0.25 wt % based on polymer.

Examples 6-11

The procedure of Example 5 was replicated to determine the reproducibility of the process. The PO3G polymer used in these examples had a molecular weight of 2449, initial color of 145 APHA, and contained 200 micrograms BHT/g polymer. The results are shown in Table 2.

TABLE 2

PO3G Color Reproducibility

| Example | Wt % Activated Carbon | Color APHA |
| --- | --- | --- |
| Control | 0 | 145 |
| 6 | 0.25 | 106 |
| 7 | 0.25 | 104 |
| 8 | 0.25 | 106 |
| 9 | 0.25 | 109 |
| 10 | 0.25 | 107 |
| 11 | 0.25 | 109 |

The data in Table 2 show the reproducibility of the color reduction with activated carbon is approximately ±3 APHA units, comparable to the replicated reproducibility of measurements on a single sample.

Example 12

The procedure of Example 5 was repeated using 2.5 kg PO3G (MW=2170; Color=126 APHA) and 62.5 g Darco G-60 activated carbon in a 3-L filtration unit. During filtration process, polymer was collected at different times, the color was measured for each fraction, and the results are shown in Table 3.

TABLE 3

PO3G Color Reduction, Larger Scale

| PO3G | Color APHA |
| --- | --- |
| Before carbon treatment | 126 |
| First fraction | 87 |
| Second fraction | 88 |
| Third fraction | 87 |
| Fourth fraction | 89 |

Examples 13-17

Example 5 was repeated using higher amounts of carbon using PO3G polymer having 2212 molecular weight and color of 70 APHA.

TABLE 4

Effect of carbon amount on PO3G color

| Example | Wt % Activated carbon | Color APHA | % change |
| --- | --- | --- | --- |
| Control | 0 | 70 | — |
| 13 | 0.25 | 52 | 25.7 |
| 14 | 1.0 | 42 | 40.0 |
| 15 | 2.0 | 39 | 44.3 |
| 16 | 3.0 | 35 | 50.0 |
| 17 | 5.0 | 34 | 51.4 |

The polymer was filtered at 70° C. to separate it from the carbon. The data in Table 4 indicate at higher levels of carbon (3 wt %) the polymer color was reduced to 50% of the initial value.

Example 18

Example 5 was repeated with the crude polymer rather than purified polymer. The crude polymer has color of 134 APHA. This polymer was hydrolyzed, neutralized with excess of calcium hydroxide and dried. A 0.25 wt % activated carbon was added to the dried PO3G polymer containing residual base and salts and filtered as described above. The filtered PO3G color was measured and found to be 80 APHA, indicating the activated carbon can be added just prior to final filtration step of the purification process.

Examples 19-24

Several different grades and forms of activated carbon were used at a fixed amount (2 wt %) to treat PO3G polymer (MW, 2070 and initial color, 92 APHA) and the results are reported in Table 5.

TABLE 5

| | Example | | | | | |
|---|---|---|---|---|---|---|
| | 19 | 20 | 21 | 22 | 23 | 24 |
| Manufacturer | Norit American | Norit American | CALGON | CALGON | CALGON | CECA |
| Grade | DARCO-G60 | NORIT RO 0.8 | PWA | BL | WPH | ACTICARBONE ENO |
| Carbon form | Powder | Pellets | Powder | Powder | Powder | Powder |
| Iodine number, mg/g | NA | 1050 | 900 | 1000 | 800 | NA |
| PO3G color, APHA | 52 | 77 | 56 | 61 | 53 | 48 |
| % change in color | 43.5 | 16.3 | 39.1 | 33.7 | 42.4 | 47.8 |

The data in Table 5 indicate all of the carbon treatments effectively reduced the PO3G polymer color from 92 to 48-77 APHA and this corresponds to a reduction in color of 47.8%-16.3%. The data also show that amount of each type of activated carbon can be varied to obtain a desired change in color.

What is claimed is:

1. A process consisting of contacting PO3G having an initial color with an adsorbent consisting of activated carbon and separating the PO3G and activated carbon, wherein the PO3G, after contact with the activated carbon, has an APHA color lower than the initial color wherein the PO3G is contacted with about 0.1 to about 5 weight % of the activated carbon based on the weight of the PO3G.

2. The process of claim 1, wherein the PO3G has a molecular weight of about 250 to about 10,000.

3. The process of claim 1, wherein the PO3G has a molecular weight of about 500 to about 5000.

4. The process of claim 1, wherein the PO3G has a molecular weight of about 500 to about 4000.

5. The process of claim 1, wherein the PO3G is contacted with about 0.25 to about 3 weight % of the activated carbon based on the weight of the PO3G.

6. The process of claim 1, wherein the contacting is conducted at a temperature of about 100 to about 150° C.

7. The process of claim 1, wherein the contacting is conducted at a temperature of about 25° to about 100° C.

8. The process of claim 1, wherein the contacting is conducted for a period of about 5 to about 60 minutes.

9. The process of claim 1, wherein the contacting is conducted for a period of about 10 to about 30 minutes.

10. The process of claim 1, wherein the PO3G has an initial APHA color of at least 50.

11. The process of claim 1, wherein the PO3G has an initial APHA color of about 70 to about 300.

12. The process of claim 1, wherein the APHA color is reduced by at least about 10%.

13. The process of claim 1, wherein the APHA color is reduced by at least about 30% as compared to the initial APHA color.

14. The process of claim 1, wherein the APHA color is reduced by at least about 50% as compared to the initial color.

15. A process consisting of:
   a. providing reactant comprising 1,3-propanediol and polycondensation catalyst;
   b. polycondensing the reactant to PO3G having an initial color;
   c. contacting the PO3G with activated carbon; and
   d. separating the PO3G and activated carbon,
such that the PO3G, after contact with the activated carbon, has a APHA color lower than the initial color herein the PO3G is contacted with about 0.1 to about 5 weight % of the activated carbon based on the weight of the PO3G, and then contacting is conducted at a temperature of about 100 to about 150° C.

16. A process consisting of contacting PO3G with activated carbon and separating the PO3G and activated carbon, wherein the PO3G has an initial APHA color, before contact with activated carbon, of about 70 to about 300, wherein the PO3G, after contact with the activated carbon, has an APHA color that is reduced by at least 10% as compared with the initial APHA color wherein the PO3G is contacted with about 0.1 to about 5 weight % of the activated carbon based on the weight of the PO3G.

* * * * *